US00PP17278P2

(12) United States Plant Patent
Trees

(10) Patent No.: US PP17,278 P2
(45) Date of Patent: Dec. 12, 2006

(54) ***GERANIUM* PLANT NAMED 'BALGALBRISE'**

(50) Latin Name: *Pelargonium×hortorum×Pelargonium peltatum*
Varietal Denomination: Balgalbrise

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 12 days.

(21) Appl. No.: 11/272,115

(22) Filed: Nov. 10, 2005

(51) Int. Cl.
*A01H 5/00* (2006.01)

(52) U.S. Cl. ..... Plt./324
(58) Field of Classification Search ..... Plt./324
See application file for complete search history.

(56) References Cited

PUBLICATIONS

European Plant Breeders' Rights application No. 2005/1964 filed Oct. 24, 2005.

*Primary Examiner*—Kent Bell
(74) *Attorney, Agent, or Firm*—Audrey Charles

(57) ABSTRACT

A new and distinct cultivar of *Geranium* plant named 'Balgalbrise' characterized by its semi-double red-colored flowers, medium green-colored foliage with a slightly darker green-colored zone, and moderately vigorous and semi-trailing growth habit.

2 Drawing Sheets

Latin name of genus and species of plant claimed: *Pelargonium×hortorum×Pelargonium peltatum.*
Variety denomination: 'Balgalbrise'.

BACKGROUND OF THE INVENTION

The present invention relates to a new and distinct cultivar of *Geranium* plant botanically known as *Perlargonium×hortorum×Pelargonium peltatum* and hereinafter referred to by the cultivar name 'Balgalbrise'.

The new cultivar originated in a controlled breeding program in California during January 2000. The object of the breeding program is to develop new interspecific *Geranium* cultivars with outwardly spreading growth habit, uniform flowering, and interesting flower and foliage colors.

The new cultivar is an irradiation induced sport of 'Sunrise', U.S. Plant Pat. No. 10,139, characterized by its single coral red-colored flowers, medium green-colored foliage with slight zonation, excellent basal branching, and medium vigorous and trailing growth habit. The irradiation occurred on Jan. 15, 2000. The new cultivar was discovered and selected by the inventor on Nov. 11, 2000 in a controlled environment at Arroyo Grande, Calif.

Asexual reproduction of the new cultivar by terminal stem cuttings since November 2000 at Arroyo Grande, Calif. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balgalbrise' as a new and distinct cultivar of *Geranium* plant:

1. Semi-double red-colored flowers;
2. Medium green-colored foliage with a slightly darker green-colored zone; and
3. Moderately vigorous and semi-trailing growth habit.

Plants of the new cultivar differ from plants of the parent primarily in flower form and flower color.

Of the many commercially available *Geranium* cultivars known to the inventor, the most similar in comparison to the new cultivar is 'Balgalsusi', U.S. Plant Pat. No. 12,457. However, in side by side comparisons, plants of the new cultivar differ from plants of 'Balgalsusi' in the following characteristic: Plants of the new cultivar have a different flower color from plants of 'Balgalsusi'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balgalbrise'. The plants were grown in 10 cm pots for 9 weeks in a greenhouse at West Chicago, Ill.

DETAILED BOTANICAL DESCRIPTION

Figure 1:
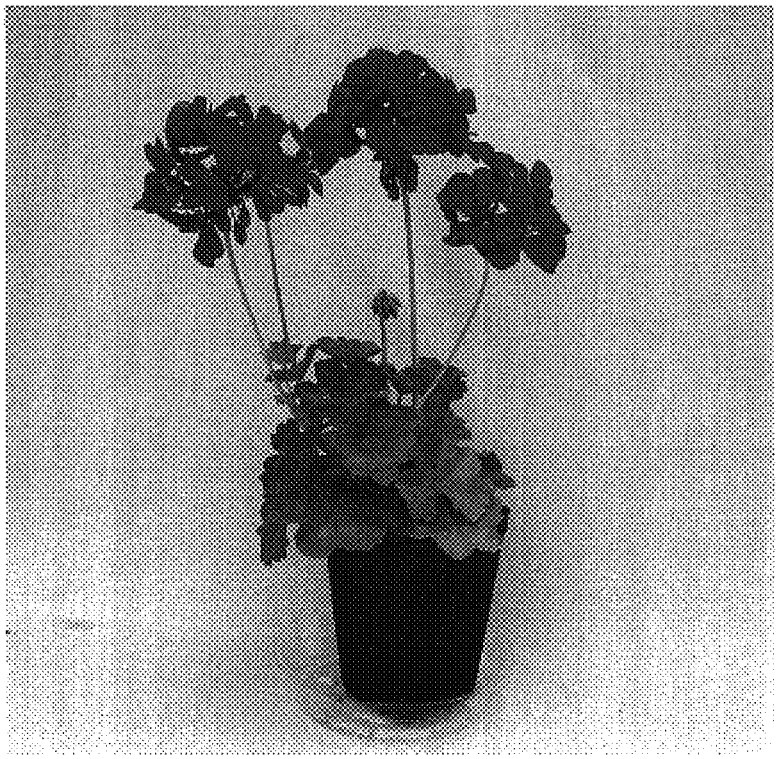
FIG. 1 illustrates a side view of the overall growth and flowering habit of 'Balgalbrise'.
Figure 2:
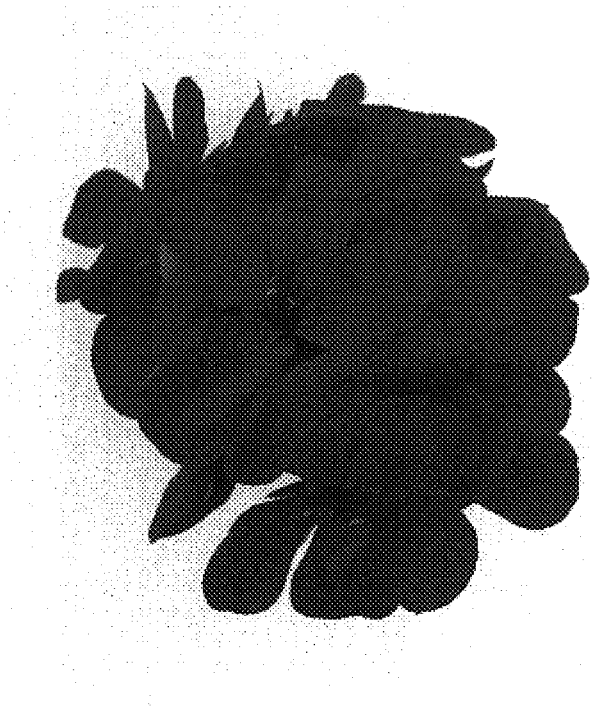
FIG. 2 illustrates a close-up view of a single umbel of 'Balgalbrise'.
Figure 3:
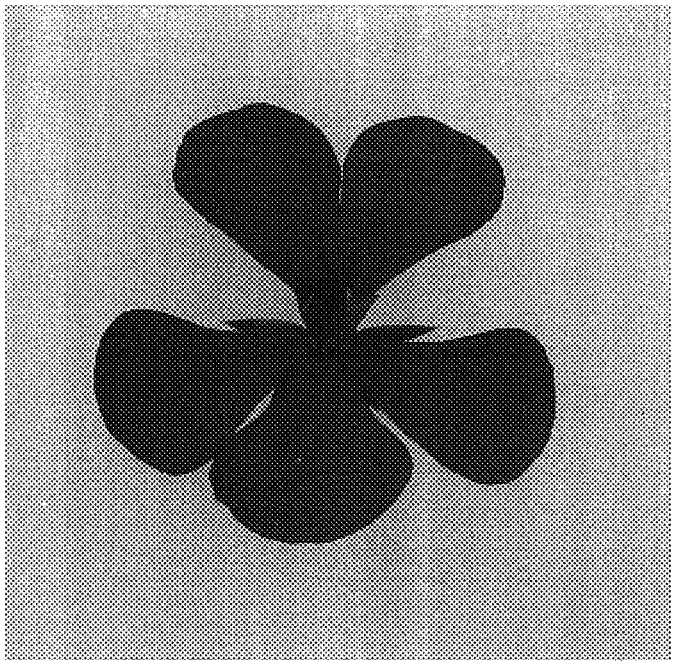
FIG. 3 illustrates a close-up view of a single flower of 'Balgalbrise'.
Figure 4:
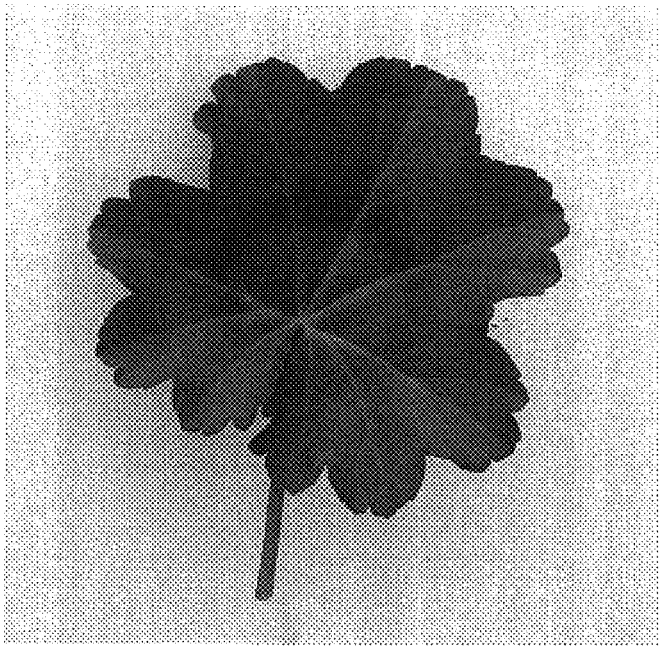
FIG. 4 illustrates a close-up view of a single leaf of 'Balgalbrise'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 16, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 9 weeks utilizing a soilless growth medium. Greenhouse temperatures were maintained at approximately 65° F. to 75° F. (18° C. to 24° C.) during the day and approximately 62° F. to 68° F. (17° C. to 20° C.) during the night. Greenhouse light levels of 3,500 to 5,000 footcandles were maintained during the day.

Botanical classification: *Pelargonium×hortorum×Pelargonium peltatum* cultivar Balgalbrise.

Parentage:

*Parent.*—'Sunrise', U.S. Plant Pat. No. 10,139.

Propagation:

*Type cutting.*—Terminal stem.

*Time to initiate roots.*—Approximately 10 to 14 days.

*Time to produce a rooted cutting.*—Approximately 21 to 28 days.

*Root description.*—Fibrous.

*Rooting habit.*—Freely branching.

Plant description:

*Crop time.*—Approximately 8 to 9 weeks from a rooted cutting.

*Growth habit and general appearance.*—Moderately vigorous and semi-trailing.

*Size.*—Height from soil level to top of plant plane: Approximately 25.6 cm. Height from soil level to top of foliage: Approximately 10.7 cm. Width: Approximately 23.6 cm.

*Branching habit.*—Freely basal branching. Approximately 2 branches per plant.

*Branch.*—Strength: Strong. Length: Approximately 9.6 cm. Diameter: Approximately 4.9 mm. Texture: Densely pubescent with short, soft hairs. Color: Closest to 144A. Internode length at center of branch: Approximately 1.9 cm.

*Foliage.*—Number of leaves per lateral branch: Approximately 10. Fragrance: None. Form: Simple. Arrangement: Opposite. Aspect: Petiole is at acute angle to stem and blade is perpendicular to stem. Shape: Reniform. Margin: Crenate, palmately lobed. Apex: Obtuse. Base: Cordate. Venation pattern: Palmate. Length of mature leaf: Approximately 4.7 cm. Width of mature leaf: Approximately 8.0 cm. Texture of upper surface: Glabrous. Texture of lower surface: Moderately pubescent with short, stiff hairs and densely pubescent along venation. Color of mature foliage upper surface: 137B with venation of 143C and with narrow, circular zone of 137A in middle of leaf. Color of mature foliage lower surface: 137C with venation of 137C. Petiole length: Approximately 4.1 cm. Petiole diameter: Approximately 2.2 mm. Petiole texture: Densely pubescent with short, soft hairs on both upper and lower surface. Petiole color: Closest to 144A.

Flowering description:

*Flowering habit.*—'Balgalbrise' is freely flowering under outdoor growing conditions with substantially continuous blooming from spring through autumn and year round in greenhouse environment.

*Time to first flower.*—Approximately 11 weeks from sticking of unrooted cutting.

*Lastingness of individual floret.*—Approximately 5 to 7 days.

Inflorescence description:

*Type.*—Umbel. Position: Above foliage. Number of open umbels at nine weeks: Approximately 2. Number of developing umbels at nine weeks: Approximately 3. Umbel diameter: Approximately 10.5 cm. Umbel height/depth: Approximately 7.3 cm. Number of flowers per umbel: Approximately 13. Fragrance: None.

*Peduncle.*—Strong, erect. Length: Approximately 18.1 cm. Diameter: Approximately 3.0 mm. Texture: Densely pubescent with moderately stiff hairs. Color: Closest to 144A.

Flower description:

*Bud rate of opening.*—Generally takes 3 to 5 days for bud to progress from first color to fully open floret.

*Bud just before opening.*—Shape: Elliptic. Length: Approximately 1.8 cm. Diameter: Approximately 7.4 mm. Petal color: 44B. Sepal texture: Densely pubescent. Petal texture: Glabrous.

*Corolla.*—Form: Semi-double. Shape: Round. Diameter: Approximately 5.2 cm. Depth: Approximately 2.0 cm.

*Petals/petaloids.*—Quantity: Approximately 6 petals and 1 to 3 irregular shaped petaloids per flower. Appearance: Dull, velvety. Aspect: Upper petals turn backward and lower petals are slightly cupped. Arrangement: Upper petals overlap and lower petals overlap but upper petals do not overlap lower petals. Shape: Obovate. Apex: Obtuse. Base: Attenuate. Margin: Entire. Texture of upper and lower surface: Glabrous. Upper petal length: Approximately 3.4 cm. Upper petal width: Approximately 2.2 cm. Lower petal length: 3.0 cm. Lower petal width: 2.2 cm. Color of upper surface of upper petal: Closest to but brighter than 42A with strong venation in lower half of 59C. Color of lower surface of upper petal: Closest to 43A with venation at base of 64B. Color of upper surface of lower petal: Closest to but brighter than 42A with slight venation at base of 59C. Color of lower surface of lower petal: Closest to 43A with venation at base of 64B.

*Pedicel.*—Strength: Strong, knobs observed at base. Angle: Acute. Length: Approximately 2.7 cm. Diameter: Approximately 1.2 mm. Texture: Densely pubescent with long, soft hairs. Color: 144A with overlay of 187B.

*Calyx.*—Shape: Five-pointed star. Width: Approximately 2.5 cm.

*Sepals.*—Quantity per floret: 5. Shape: Lanceolate. Apex: Acuminate. Margin: Entire. Upper sepal length: Approximately 1.6 cm. Upper sepal width: Approximately 4.7 mm. Lower sepal length: Approximately 1.5 cm. Lower sepal width: Approximately 2.9 mm. Texture of upper surface: Glabrous. Texture of lower surface: Densely pubescent with long, soft hairs. Color of upper and lower surfaces: 144B with overlay of 187B.

*Reproductive organs.*—Androecium: Quantity of mature anthers: Approximately 4 per flower. Anther shape: Oblong. Anther length: Approximately 2.3 mm. Anther color: 59A. Pollen amount: Moderate. Pollen color N163A. Gynoecium: Pistil quantity: One per floret. Pistil length: Approximately 1.3 cm. Stigma shape: Five branched. Stigma length: Approximately 4.0 mm. Stigma color: 53C. Style length: Approximately 4.0 mm. Style color: 67B. Ovary length: Approximately 5.0 mm. Ovary texture: Sericeous. Ovary color: 144C.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'Balgalbrise', substantially as herein shown and described.

* * * * *